United States Patent [19]

Fleet et al.

[11] Patent Number: 4,849,430

[45] Date of Patent: Jul. 18, 1989

[54] METHOD OF INHIBITING VIRUS

[75] Inventors: George W. J. Fleet; Thomas W. Rademacher; Raymond A. Dwek, all of Oxford, United Kingdom

[73] Assignee: Monsanto Company, St. Louis, Mo.

[21] Appl. No.: 248,461

[22] Filed: Sep. 23, 1988

Related U.S. Application Data

[63] Continuation-in-part of Ser. No. 166,065, Mar. 9, 1988, abandoned, which is a continuation-in-part of Ser. No. 136,224, Dec. 21, 1987, abandoned.

[51] Int. Cl.$^4$ .............................................. A61K 31/445
[52] U.S. Cl. ..................................................... 514/315
[58] Field of Search ......................................... 514/315

[56] References Cited

U.S. PATENT DOCUMENTS

| | | | |
|---|---|---|---|
| 4,065,562 | 12/1977 | Ohata et al. | 424/267 |
| 4,182,767 | 1/1980 | Morai et al. | 424/267 |
| 4,639,436 | 1/1987 | Junge et al. | 514/24 |

FOREIGN PATENT DOCUMENTS

WO87/03903 7/1987 PCT Int'l Appl. .

OTHER PUBLICATIONS

Sunkara et al., Biochem. Biophys. Res. Commun. 148(1), 206–210 (1987).
Tyms et al., Lancet, Oct. 31, 1987, pp. 1025–1026.
Walker et al., Proc. Natl. Acad. Sci. USA 84, 8120–8124 (1987).
Gruters et al., Nature, 74–77 (1987).
Fleet et al., FEBS Lett. 237, 128–132 (1988).
Schweden et al., Arch. Biochem. Biophys. 248(1), 335–340 (1986).
Fleet et al., Tetrahedron Lett. 26(26), 3127–3130 (1985).
Fleet et al., Chemistry Lett. 1051–1054 (1986).
Fung et al., Bio/Technology 5, 940–946 (1987).
Karpas et al., Leuk. Res. 1, 35–49 (1987).
Karpas et al., Lancet, Jul. 18, 1987, pp. 132–133.
Karpas et al., Mol. Biol. Med. 1, 457–459 (1983).
Romero et al., FEBS Lett. 183(1) 29–32 (1985).
Saul et al., Arch. Biochem. Biophys. 221(2), 593–597 (1983).
Elbein, Ann. Rev. Biochem. 56, 497–534 (1987).
Elbein, Meth. Enzymol. 138, 661–709 (1987).
Fuhrmann, et al., Biochim. Biophys. Acta 825, 95–110 (1985).

*Primary Examiner*—Jerome D. Goldberg
*Attorney, Agent, or Firm*—Scott J. Meyer; James W. Williams, Jr.

[57] ABSTRACT

A method of inhibiting human immunodeficiency virus is disclosed which comprises administering to a patient infected with said virus a virally inhibitory effective amount of the N-butyl derivative of deoxynojirimycin or a pharmaceutically acceptable salt derivative thereof.

1 Claim, 5 Drawing Sheets

METHOD OF INHIBITING VIRUS

CROSS-REFERENCE TO RELATED APPLICATION

This is a continuation-in-part of copending application Ser. No. 166,065, filed Mar. 9, 1988, now abandoned, which in turn is a continuation-in-part of application Ser. No. 136,224, filed Dec. 21, 1987, now abandoned.

BACKGROUND OF THE INVENTION

This invention relates to a method of inhibiting human immunodeficiency virus (HIV) and, more particularly, to the N-butyl derivative of 1,5-dideoxy-1,5-imino-D-glucitol (deoxynojirimycin) having potential use for the treatment of acquired immune deficiency syndrome (AIDS).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+T-cells (or CD4+cells). See, e.g., Gallo et al., *Science* 224, 500–503 (1984), and Popovic et al., Ibid., 497–500 (1984). This retrovirus had been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more recently isolated by Montagnier and his coworkers in 1986 [*Nature* 326, 662 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

More recently, certain glycosidase inhibitors have been tested for activity against the AIDS virus. Three such compounds suggested as potential anti-AIDS drugs are castanospermine, 1-deoxynojirimycin (DNJ) and 2,5-dihydroxymethyl-3,4-dihydroxy-pyrrolidine (DMDP). See, e.g., Sunkara et al., *Biochem. Biophys. Res. Commun.* 148(1), 206–210 (1987); Tyms et al., *Lancet,* Oct. 31, 1987, pp. 1025–1026; Walker et al., *Proc. Natl. Acad. Sci. USA* 84, 8120–8124(1987); and Gruters et al., *Nature* 330, 74–77 (1987).

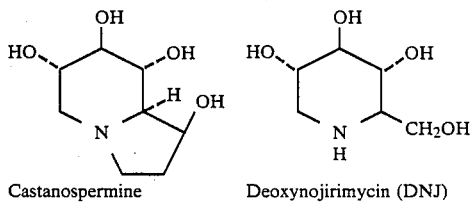

Castanospermine

Deoxynojirimycin (DNJ)

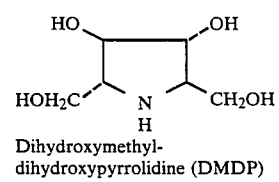

Dihydroxymethyl-dihydroxypyrrolidine (DMDP)

Thus, castanospermine, which is an alkaloid isolated from the seeds of Australian chestnut tree, has been found to interfere with normal glycosylation of HIV virions, thereby altering the envelope glycoprotein and preventing entry of HIV into target cells. However, only a modest reduction in virion infectivity was found.

In PCT Inter. Appln. WO 87/03903, published July 2, 1987, the N-methyl derivative of deoxynojirimycin (DNJ) also was dictated as having activity against HIV ostensibly based on its glucosidase I inhibitory activity. However, it was subsequently shown by Fleet et al., *FEBS Lett,* In Press, 1988, that not all glucosidase I inhibitors are effective inhibitors of HIV. Therefore, some other mechanism may be responsible for HIV inhibitory activity.

BRIEF DESCRIPTION OF THE INVENTION

In accordance with the present invention the N-butyl derivative of deoxynojirimycin has been found to have substantially enhanced inhibitory activity against the human immunodeficiency virus (HIV) at non-toxic concentrations compared to that exhibited by the corresponding N-methyl and N-ethyl derivatives. The N-butyl-deoxynojirimycin uniquely reduces the virus titer by over five logs at non-cytotoxic concentrations whereas the N-methyl- and N-ethyldeoxynojirimycin derivatives cause only a two to four log-order of reduction in the yield of infectious HIV. As such, the N-butyl derivative has exceptional and significant potential use for the treatment of acquired immune deficiency syndrome (AIDS). This outstanding HIV inhibitory activity was surprising and unexpected, if and only if glucosidase I inhibitory activity is the operative mechanism, since the glucosidase I inhibitory activity of the N-methyl and N-butyl derivatives of deoxynojirimycin was reported to be virtually identical by Schweden et al., *Arch. Biochem. Biophys.* 248(1), 335–340 (1986).

The N-butyl derivative of deoxynojirimycin has the following chemical structure:

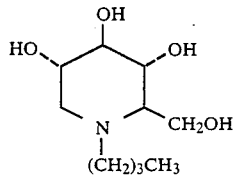

In order to indicate stereoisomerism, solid and dotted lines show bonds directed above or below, respectively, the plane of the paper.

DETAILED DESCRIPTION OF THE INVENTION

Figure 1:
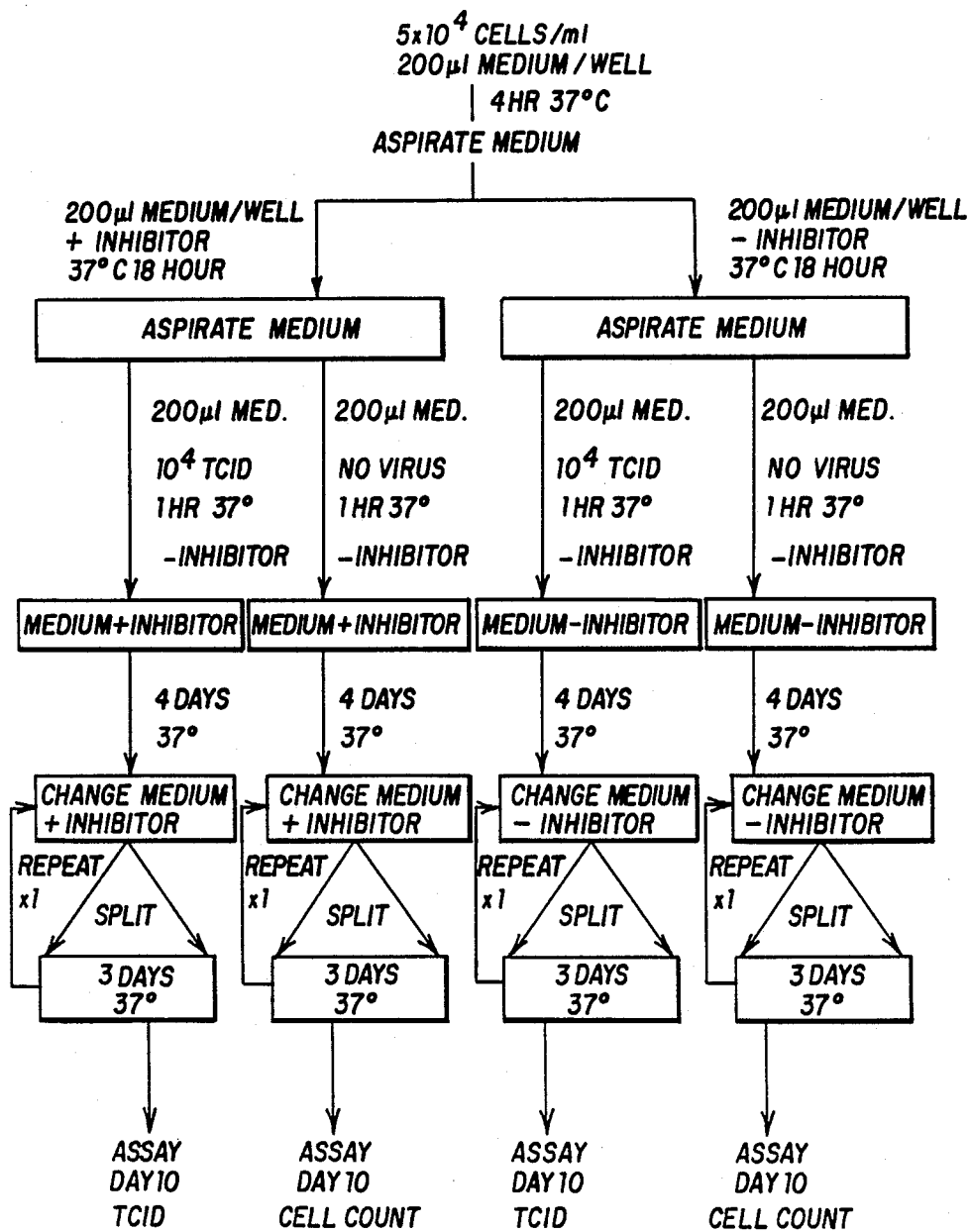

While the specification concludes with claims particularly pointing out and distinctly claiming the subject matter regarded as forming the invention, it is believed that the invention will be better understood from the following description taken in conjunction with the accompanying drawings in which:

FIG. 1 is a schematic outline of the test procedure used to assess the cytotoxic effect of test compounds on T-cells either infected or non-infected with HIV and in parallel the HIV inhibitory activity of the test compounds. TCID is the tissue culture infectious dose. Cells were cultured in RPMI-1640 medium with 10% fetal calf serum containing 100 units/ml penicillin G and 100 μg/ml streptomycin.

Figure 2:
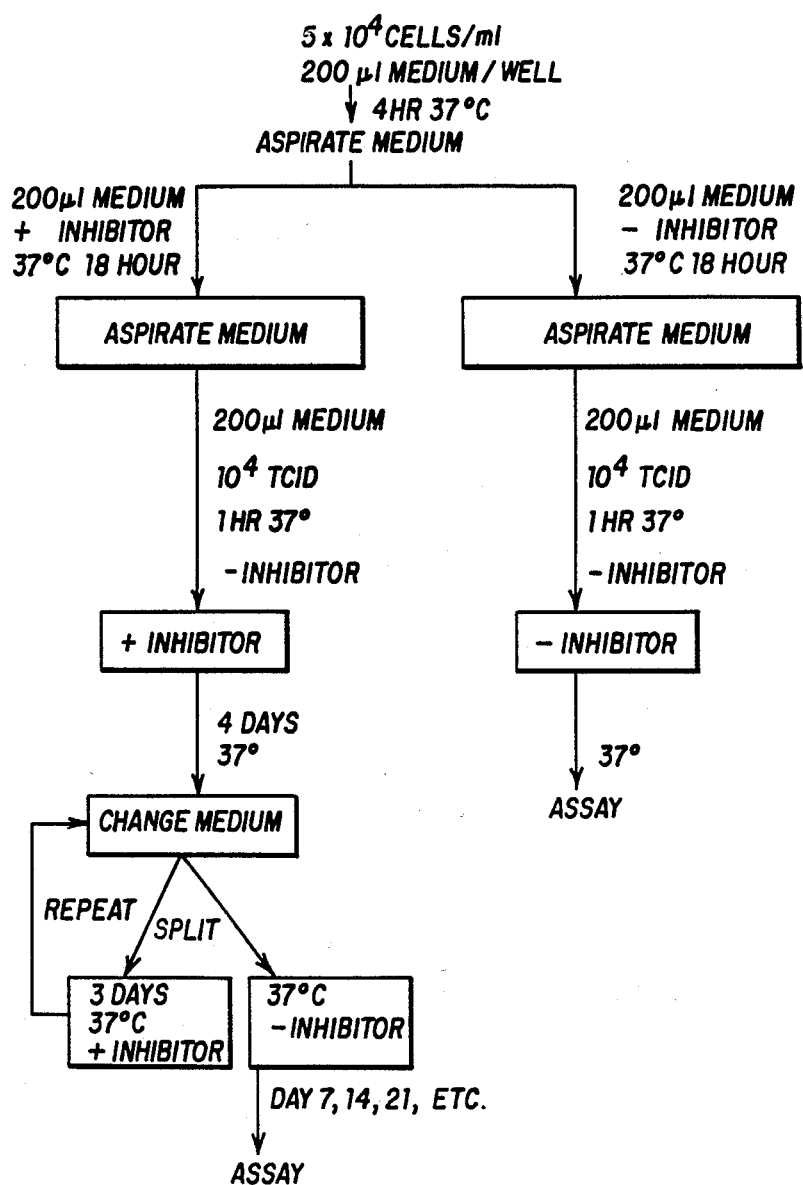

FIG. 2 is a schematic outline of the test procedure used to determine the relative proportion of HIV-infected cells in cultures containing 0.1 mg/ml of the inhibitory test compound. At various times aliquots of the infected cell suspensions were transferred to inhibitor-free medium and the time taken for the cells to develop cytopathic effect (CPE) was recorded.

Figure 3:
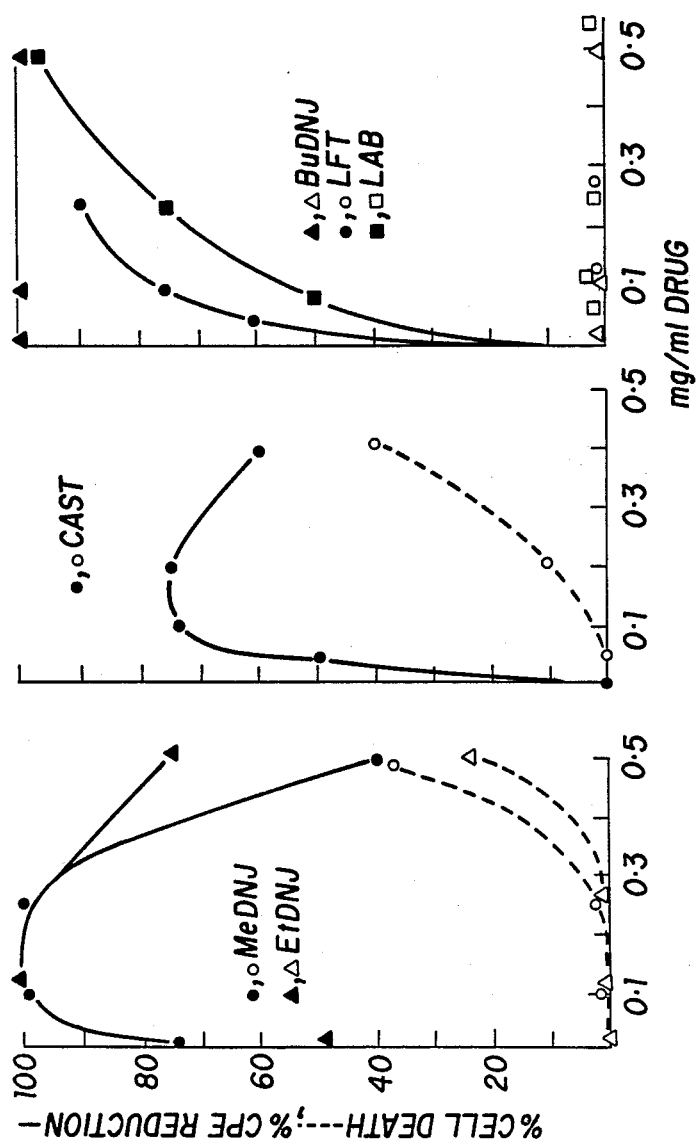

FIG. 3 is a graphical representation in which the inhibition of HIV associated CPE (——— % CPE) reduction) and test compound-associated cytotoxicity (- - - - - % cell death) is plotted against the media concentration in mg/ml of several test compounds (drugs). The cell viability data was determined for non-HIV infected cells. The test compounds were the N-methyl-, N-ethyl-, and N-butyl derivatives of deoxynojirimycin (DNJ), castanospermine (Cast), N-(5-carboxymethyl-1-pentyl)-1,5-imino-L-fucitol (LFT) and 1,4-dideoxy-1,4-imino-L-arabinitol (LAB).

Figure 4:
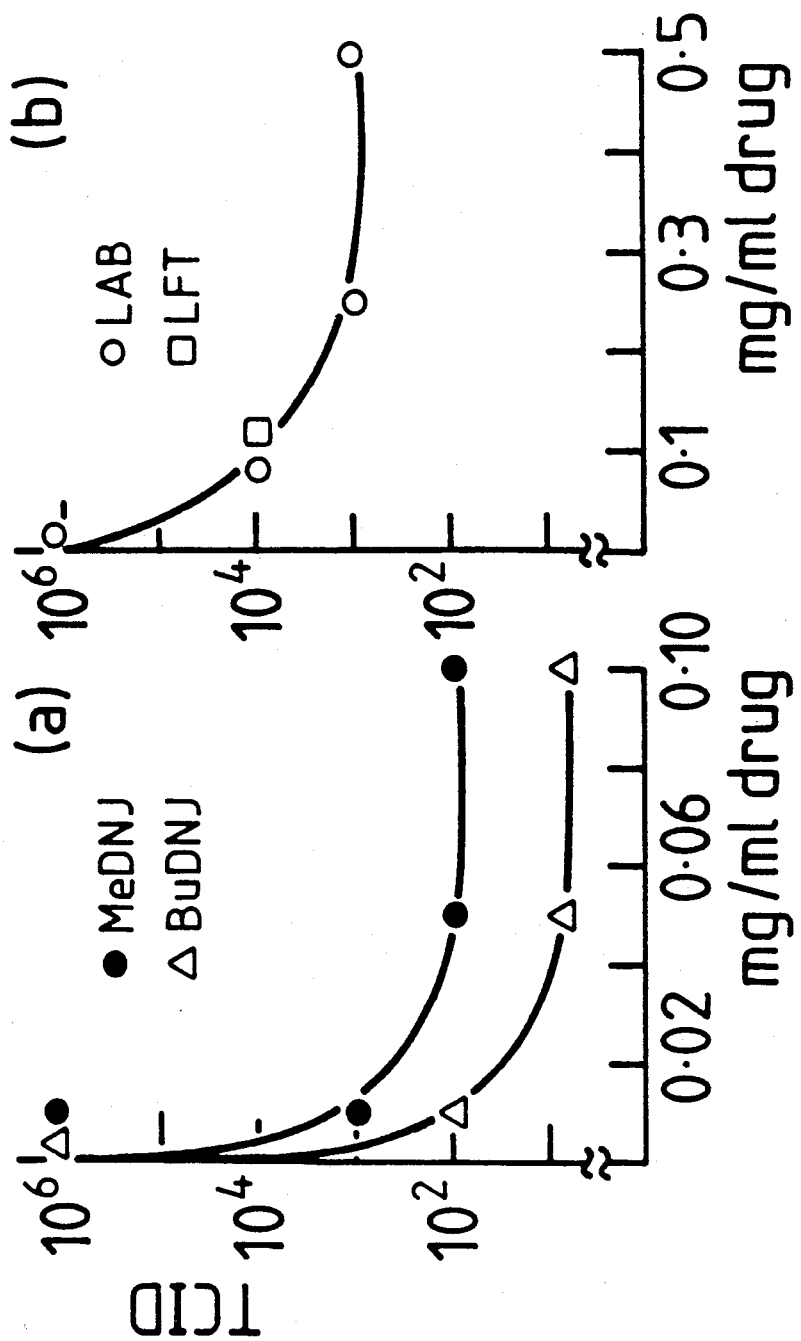

FIG. 4 is a graphical representation in which the viral titer (determined as TCID) is plotted against the concentration in mg/ml of various of the test compounds (drugs) of FIG. 3 in panels (a) and (b).

Figure 5:
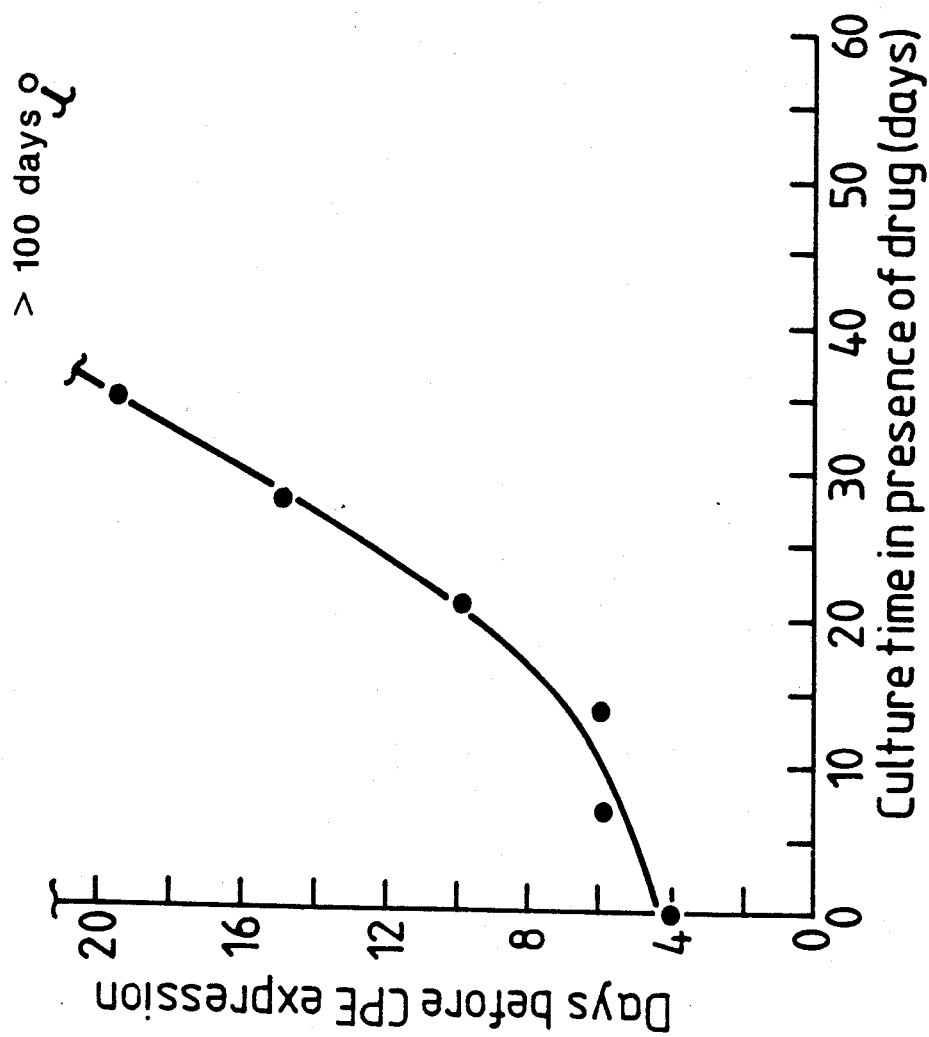

FIG. 5 is a graphical representation which shows the relationship between the time taken from HIV infected cells grown in the presence of 0.1 mg/ml N-butyl-deoxynojirimycin (drug) to develop CPE once drug-free medium was used (days before CPE expression) and culture time in presence of the drug in days. After 55 days of culture (O) in the presence of drug no virus appeared during 100 additional days of culture in the absence of drug (after removal of drug).

The N-butyl derivative of deoxynojirimycin is a known compound. It can be prepared by the N-butylation of 1,5-dideoxy-1,5-imino-D-glucitol (deoxynojirimycin). Methods of preparation are described, for example, in U.S. Pat. Nos. 4,182,767 and 4,639,436.

The effectiveness of the active N-butyldeoxynojirimycin in the method of the invention has been demonstrated by positive inhibitory activity toward replication of the HIV in vitro. In accordance with this assay system, human T cells which are susceptible to HIV infection were used to visually determine the relative activity of several test compounds to inhibit replication of the HIV infected cells. Since various analogous compounds had substantially divergent results as described hereinafter, it is apparent that the effectiveness of any given compound as an inhibitor of HIV is unpredictable. Various theories have been proposed heretofore with respect to the effect of prior art HIV inhibitors. Research at several laboratories has established that interaction between the envelope glycoprotein, gp120, and some part of the CD4 antigen is involved in the recognition of HIV and most of the cells it infects and the binding of HIV to those cells. Thus, in one report which compared the positive effect of the glycosidase inhibitor deoxynojirimycin (DNJ) upon HIV infectivity against the absence of effect of the mannosidase I inhibitor deoxymannojirimycin (DMJ), which is the 2-epimer of DNJ, it was suggested that the perturbed carbohydrate structure of the gp120 or its precursor, imposed by the blocking of the N-linked oligosaccharide trimming pathway, is responsible for the effect. Gruters et al., Nature 330, 74–77 (1987).

The unpredictable effect of a test compound against HIV is demonstrated by several comparative studies of structurally analogous sugar derivatives. For example, while the known inhibition of the cytopathic effect (CPE) by the α-glucosidase I inhibitor castanospermine is confirmed, neither the epimer L-1, 6-diepicastanospermine nor the stereoisomer of castanospermine, L-6-epicastanospermine, were found to be inhibitory. See Fleet et al., FEBS Lett., In Press, 1988.

So also, although both enantiomers of 1,4-dideoxy-1,4-imino-arabinitol are known glucosidase inhibitors [Fleet et al., Tetrahedron Lett. 26, 3127–3130(1985); Fleet et al., Chemistry Lett. 1051–1054(1986)]; the L-enantiomer has strong HIV inhibitory activity [see also copending application Ser. No. 136,219, filed Dec. 21, 1987] whereas the D-enantiomer has very little effect on HIV replication. For both enantiomers, N-methylation reduced rather than increased anti-HIV activity. Neither the azofuranose analog of glucose nor the N-benzyl derivative were found to have an effect on CPE. Similarly, no HIV inhibition was observed for fagomine, the 2-deoxyglucose analog, although it too is known to have α-glycosidase inhibitory activity. See Fleet et al., FEBS Lett., In Press, 1988.

The inhibitory activity of the N-butyldeoxynojirimycin of this invention toward HIV relative to the inhibitory activity of analogous test compounds is specifically demonstrated herein by an in vitro assay system in which T-cells are grown in suitable nutrient culture medium and exposed to HIV inoculum in the presence or absence of test compound and compared with control cells which are grown in culture medium alone. After a suitable period of incubation, the cultures are scored for the presence of so-called syncytial cells (giant cells). Typical examples of such a test for the evaluation of inhibitors of HIV have been disclosed by Fung et al., Bio/Technology 5, 940–946 (1987); Tyms et al., Lancet, Oct. 31, 1987, pp. 1025–1026; Gruters et al., Nature 330, 74–77 (1987); and Walker et al., Proc. Natl. Acad. Sci. USA 84, 8120–8124 (1987).

In the present case, a human leukemic T-cell line was used which is described by Karpas, Leuk. Res. 1, 35–49 (1977). This cell line (T-45) was established from a child with acute lymphoblastic leukemia. Another T-cell line used to demonstrate the inhibitory activity of the N-butyl-deoxynojirimycin is the MOLT-4 cell line. This cell line was originally derived from the peripheral blood of a patient with acute lymphoblastic leukemia. Further information on the origin and characteristics of this cell line can be had by reference to Minowada, *J. Natl. Cancer Inst.* 49, 891–895 (1972). The MOLT-4 cell line is on deposit without restriction in the permanent collection of the American Type Culture Collection, Rockville, Maryland, under accession number ATCC CRL 1582. Samples of the cell line can be obtained by the public upon request to that depository.

Cell free suspensions of the HIV were prepared from infected cultures. The concentration of infectious particles was estimated on end-point titration assay using serial ten-fold dilutions. The approximate number of infectious particles in each preparation was determined by the highest dilution which contains infectious HIV as determined by synctial formation, cytophaticity [Leonard et al., *Proc. Natl. Acad. Sci. USA* 85, 3570–3574 (1988); Barre-Sinoussi et al., Science 220, 868–870 (1983)] and HIV antigen [Karpas et al., Lancet 1, 695–697 (1985)] synthesis after 10 days of culture with $10^4$ T-cells. This represents the concentration of infectious particles, herein defined as the tissue culture infectious dose (TCID).

The assay was run in 96 well plastic microtiter plates in which 0.2 ml of culture medium containing $10^4$ T-cells are seeded into each well. RPMI-1640 supplemented with 10% fetal calf serum was used as the culture medium. In each assay, 6 wells are used. Three (1–3) are infected with $10^4$ TCID/well of HIV-1 or HIV-2 and to the other three (4–6) culture medium alone is added. Medium is changed at the same intervals for each test compound. The detailed assay procedure is illustrated in FIGS. 1 and 2.

The following examples will illustrate the invention in greater detail although it will be understood that the invention is not limited to these specific examples or the details therein.

EXAMPLE 1

The HIV inhibitory activity of N-n-butyldeoxynojirimycin (BuDNJ) was assessed in various comparisons with the N-methyl (MeDNJ) and N-ethyl (EtDNJ) analogs and with castanospermine (Cast), 1,4-dideoxy-1,4-imino-L-fucitol (LAB) and N-(5-carboxymethyl-1-pentyl)-1,5-imino-L-fucitol (LFT), and other aminosugar derivatives mentioned hereinbefore.

The efficacy of the test compounds used in this example was assessed as follows: 0.2 ml of culture medium containing $10^4$ T-45 cells were transferred into each well of a 96-well flat-bottomed tissue-culture plastic plate and the cells were allowed to settle at 37° C. (see FIG. 1). After 4 hours the media were aspirated and replaced with media which contained the test compound. Following overnight incubation the media was aspirated and $10^4$ TCID of virus (HIV-1 or HIV-2) was added to each well. Incubation was continued at 37° C. in 5% $CO_2$ for 1 hour. Thereafter, growth media containing the various compounds were added and incubation at 37° C. was continued. Control cultures were maintained as indicated in FIG. 2. On the fourth day the cell suspensions from each well were split and seeded into two new wells and 0.2 ml of fresh media with compounds was added. This was repeated on the seventh day. Cells were examined by microscopy during days 1 to 10 for the presence of syncytia, growth rate and the appearance of the ctyopathic effect (CPE) (giant cells, pycnotic nuclei, loss of refractility). CPE (100%) was defined as no round, refractile, uniform cells remaining; only giant, ballooned pyknotic cells were present. The viability of HIV infected cultures was determined by a rough count/estimate of cells which underwent CPE in relation to round refractile uniform (normal) cells in a given culture. Cells in wells which were incubated with compounds which appeared to inhibit or reduce HIV replication and in which there was marked cell proliferation were either transferred to larger wells (of a 24-well plate) or divided in order to maintain an approximate constant cell density to promote continuous cell division.

To determine if there was a gradual reduction of HIV-infected cells in cultures maintained with BuDNJ, aliquots of cells infected with $10^4$ TCID of HIV-1 and grown in the presence of 0.1 mg/ml BuDNJ for varying lengths of time were transferred in separate wells and grown in drug-free medium as indicated in FIG. 3. The cultures were then monitored for development of CPE, indicative of active HIV replication. The times for the appearance of an advanced CPE were recorded. To confirm that HIV-1 or HIV-2 was the cause of the CPE, cells were fixed on glass slides to verify the expression of the corresponding viral antigen using the method described by Karpas et al., *Lancet* 1, 695–697 (1985). Compounds which were found to inhibit HIV-1 and HIV-2 replication in T-45 cells were subsequently used with the MOLT-4 human leukaemic T-cell line.

The results of the foregoing tests were as follows:

The effect of various concentrations of MeDNJ, EtDNJ, Cast, BuDNJ, LFT and LAB, respectively, on CPE formation as shown in FIG. 3. These data show a bell shaped dose-dependence for MeDNJ, EtDNJ and Cast. The cell viability data shown in FIG. 3 and growth rates in Table 1 for non-infected cells grown in the presence of MeDNJ, EtDNJ and Cast suggest that these compounds lack selective anti-viral activity, and are cytotoxic, as would be expected for inhibitors of oligosaccharide biosynthesis. Therefore, the apparent loss of anti-viral activity (bell shaped dose-dependence) of these drugs at high concentrations arises from the cytotoxic effect of the drugs mimicking and being scored as an HIV induced cytopathic effect. In contrast, the compounds BuDNJ, LFT and LAB showed no cytotoxicity over the concentration range used. BuDNJ completely prevented CPE in the HIV infected cells at all concentrations tested. The difference in behavior between BuDNJ and the other alkyl analogues of DNJ, (MeDNJ and EtDNJ), suggests that its mechanism of action may be different. Similarly, the $\alpha$-fucosidase inhibitor LFT which doesn't disrupt oligosaccharide biosynthesis was not found to be cytotoxic. The properties of LAB were similar to LFT. The activity of LAB as an $\alpha$-glucosidase inhibitor is reported by Fleet et al., *FEBS Lett.*, In Press, 1988, but has yet to be tested for activity against the processing $\alpha$-glucosidases (i.e. I and II). The HIV inhibitory activity of LFT and LAB is disclosed in corresponding application Ser. No. 136,219, filed Dec. 21, 1987.

Quantitative data on the effect of the various compounds on the non-infected cells (cytotoxicity) was obtained by comparison of their growth rate to control cells not exposed to drugs (Table 1). FIG. 4 and Table 2 show the relation between the TCID titre of culture supernatants of T-45 cells infected with HIV after 10 days in culture and the concentration of drug. These data show that LAB and LFT were only able to reduce the TCID partially, even at very high concentration of the drug. Similarly, DNJ, MeDNJ and EtDNJ reduced the TCID only partially, although to a greater extent than LAB and LFT. The inability of any of these drugs alone to totally reduce the TCID may be due to heterogeneity of virus production or spread. FIG. 4 and Table 2 shows that only BuDNJ was able to achieve negligible virus TCID titres at concentrations which were non-cytotoxic. These data together with the data presented in FIG. 3 suggest a viral-specific activity for this compound. Table 2 shows the results of a direct side by side comparison of the anti-viral activity (reduction in TCID) of DNJ and its derivatives against HIV-1 and HIV-2. In addition, the MOLT-4 cell line was also used. These data show that similar anti-viral activity is found against HIV-1 and HIV-2 and that this activity is not restricted to virus grown in the T-45 cell line.

In order to determine whether or not there was an actual reduction in HIV-infected cells in the presence of BuDNJ, aliquots of the infected cell suspension, grown for varying times in the presence or drug, where transferred to drug-free medium as outlined in FIG. 2. The cultures were then monitored for the development of CPE and giant cell formation (indicative of active HIV replication). The increase in the time taken for the cells to develop CPE once drug-free medium was used (FIG. 5) suggests that prolonged exposure to BuDNJ reduced the proportion of infected cells in the cultures. Whether this is viewed as either a reduction in the doubling time of the infected cells as compared to uninfected T-45 cells or as viral replication with cytolysis does not alter the conclusion that natural turnover of the cell population in vivo would eventually reduce the number of infected cells dramatically and possibly break the cycle of re-infection.

TABLE 1
CYTOTOXICITY AND T-CELL GROWTH

| Compound | Dosage (mg/ml) | Estimated Cell Growth Virus-uninfected Day 7 |
|---|---|---|
| No drug | — | $1.2 \times 10^6$ |
| DNJ | 0.50 | $1.4 \times 10^6$ |
|  | 0.25 | $1.4 \times 10^6$ |
| MeDNJ | 0.50 | $5.0 \times 10^6$ |
|  | 0.25 | $1.0 \times 10^6$ |
|  | 0.10 | $1.0 \times 10^6$ |
|  | 0.05 | $1.2 \times 10^6$ |
|  | 0.01 | $1.2 \times 10^6$ |
| EtDNJ | 0.10 | $1.3 \times 10^6$ |
|  | 0.05 | $1.2 \times 10^6$ |
|  | 0.01 | $1.2 \times 10^6$ |
| BuDNJ | 0.10 | $1.4 \times 10^6$ |
|  | 0.05 | $1.2 \times 10^6$ |
|  | 0.01 | $1.2 \times 10^6$ |
| LAB | 0.50 | $1.0 \times 10^6$ |
|  | 0.25 | $1.5 \times 10^6$ |
|  | 0.10 | $1.5 \times 10^6$ |
| Cast | 0.70 | Toxic |
|  | 0.35 | $8.0 \times 10^5$ |
|  | 0.18 | $8.0 \times 10^5$ |
|  | 0.09 | $1.0 \times 10^6$ |
|  | 0.02 | $1.2 \times 10^6$ |

TABLE 2
COMPARISION OF DNJ DERIVATIVES

| Virus | Dosage (mg/ml) | HIV-1 (TCID) | HIV-2 (TCID) |
|---|---|---|---|
| Control | — | $10^6$ | $10^6$ |
| DNJ | 0.10 | $10^5$ | $10^5$ |
| MeDNJ | 0.10 | $10^2$ | $10^2$ |
| EtDNJ | 0.10 | $10^3$ | $10^3$ |
| BuDNJ | 0.10 | $<10$ | $<10$ |

Identical results were found when either $10^4$ T-45 cells or MOLT-4 cells were treated with DNJ and its three derivatives before infecting the cells with HIV-1 and separately with HIV-2 ($10^4$ TCID). The HIV-1, which was used to infect the T-45 cell line was first passaged in T-45 cells. Likewise, HIV-1 which was used to infect MOLT-4 was first passaged in MOLT-4 cells. The same was done with HIV-2. TCID's were measured after day 10.

EXAMPLE 2

In order to particularly illustrate the HIV inhibitory activity of N-butyl-deoxynojirimycin of the invention compared to the activity of the N-methyl and N-ethyl analogs as well as the non-alkylated deoxynojirimycin and untreated controls, the following tabulation shows the results of tests carried out according to the procedure of Example 1 on both T-45 cells and MOLT-4 cells with HIV-1 and, separately, with HIV-2. That is, HIV-1 was first passaged in T-45 cells; likewise, HIV-1 was first passaged in MOLT-4 cells. The same passaging was done with HIV-2. The test compounds were used at a concentration of 0.1 mg/ml. $10^4$ TCID of HIV-1 and separately of HIV-2 were used to infect $10^4$ cells. Upon completion of the test, the virus titers were as follows:

TABLE 3

| | VIRUS TITER | | | | |
|---|---|---|---|---|---|
| | Control | DNJ | MeDNJ | EtDNJ | BuDNJ |
| HIV-1 | $10^6$ | $10^5$ | $10^2$ | $10^3$ | 10 |
| HIV-2 | $10^6$ | $10^5$ | $10^2$ | $10^3$ | 10 |

These results thus show that the N-butyl-deoxynojirimycin surprisingly is not only two log orders more effective as an inhibitor of HIV than the N-methyl-deoxynojirimycin but also three log orders more effective than the N-ethyl deoxynojirimycin in replicate tests (Tables 2 and 3) each with two virus strains in two different cell lines.

EXAMPLE 3

The N-butyl-DNJ inhibitor of the invention was further differentiated from DNJ and N-methyl-DNJ by comparing the incorporation of radiolabeled galactose, mannose, glucose and thymidine into B16-F10 murine melanoma cells following incubation of the cells with the test compound. The following results were obtained:

1. DNJ and N-butyl-DNJ each inhibited mannose utilization whereas N-methyl-DNJ either stimulated incorporation or, conservatively, had no effect.

2. DNJ and N-butyl-DNJ each substantially inhibited galactose incorporation into the cells at 1.0 mM or less whereas N-methyl-DNJ was only slightly inhibitory.

3. In glucose utilization/inhibition testing the N-methyl-DNJ had an inverted dose-response curve whereas N-butyl-DNJ had little or no effect and DNJ inhibited in a normal dose-response manner.

4. $^3$H-Thymidine uptake into the cells was not affected by N-butyl-DNJ up to 2.0 mM whereas N-methyl-DNJ inhibited incorporation at 1.0 mM and DNJ inhibited incorporation at 2.0 mM.

The antiviral agent described herein can be used for administration to patients infected with the human immunodeficiency virus by conventional means, preferably in formulations with pharmaceutically acceptable diluents and carriers. This agent can be used in the free amine form or in its salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, PA.

Various other examples will be apparent to the person skilled in the art after reading the present disclosure without departing from the spirit and scope of the invention. It is intended that all such further examples be included within the scope of the appended claims.

What is claimed is:

1. The method of inhibiting human immunodeficiency virus in a patient infected with said virus comprising administering to said patient a virally inhibitory effective amount of N-n-butyl deoxynojirimycin or a pharmaceutically acceptable salt derivative thereof.

* * * * *